(12) United States Patent
Burns

(10) Patent No.: US 8,343,464 B2
(45) Date of Patent: Jan. 1, 2013

(54) COMPOSITION AND METHOD FOR TREATING EUSTACHIAN TUBE DYSFUNCTION

(76) Inventor: Phillip E. Burns, Wilton Manors, FL (US)

( * ) Notice: Subject to any disclaimer, the term of this patent is extended or adjusted under 35 U.S.C. 154(b) by 0 days.

(21) Appl. No.: 13/094,079

(22) Filed: Apr. 26, 2011

(65) Prior Publication Data

US 2011/0268669 A1    Nov. 3, 2011

Related U.S. Application Data

(60) Provisional application No. 61/329,619, filed on Apr. 30, 2010.

(51) Int. Cl.
*A61K 9/68* (2006.01)

(52) U.S. Cl. ............ 424/48; 424/400; 424/434; 424/435

(58) Field of Classification Search ........................ None
See application file for complete search history.

(56) References Cited

U.S. PATENT DOCUMENTS

2009/0312724 A1 * 12/2009 Pipkin et al. .................. 604/294

FOREIGN PATENT DOCUMENTS

WO    WO 03077883    * 9/2003

OTHER PUBLICATIONS

DOW CORNING Q7-2587 "30% Simethicone Emulsion USP" product sheet (Dec. 4, 2005) pp. 1-2.*
Derwent abstract WO 03077883, Sep. 2003, (English, pp. 1-6).*
Machine translation of WO 03077883, Sep. 2003, pp. 1-5.*
Docherty and McCallum; Foundation Clinical Nursing Skills; Chapter 2.6 "Administration of medicines", Oxford University Press; pp. 1-15 (2009).*
Grimmer et al "Update on Eustachian Tube Dysfunction and the Patulous Eustachian Tube" from Current Opinion in Otolaryngology and Head and Neck Surgery, vol. 13, No. 5, p. 277-282 (Oct. 2005).*

* cited by examiner

*Primary Examiner* — Bethany Barham
(74) *Attorney, Agent, or Firm* — Glenn E. Gold; H. John Rizvi; Gold & Rizvi, P.A.

(57) ABSTRACT

A method of treating Eustachian tube dysfunction in a person includes placing the person's body in a position substantially lying on one of the person's left or right sides. The side on which the person is lying is the side affected by Eustachian tube dysfunction. A composition of simethicone in a concentration of about 0.05% to 0.65% wt/vol diluted in an aqueous carrier is introduced through the nasal cavity of the same side on which the person is lying. The simethicone composition is then allowed to coat the person's pharynx on the side of which the person is lying.

3 Claims, 2 Drawing Sheets

COMPOSITION AND METHOD FOR TREATING EUSTACHIAN TUBE DYSFUNCTION

CROSS-REFERENCE TO RELATED APPLICATION

This Non-Provisional Utility application claims the benefit of U.S. Provisional Patent Application Ser. No. 61/329,619, filed on Apr. 30, 2010, which is incorporated herein in its entirety.

FIELD OF THE INVENTION

The present disclosure generally relates to methods for treating Eustachian tube dysfunction. More particularly, the present disclosure relates to the pharyngeal introduction of a simethicone emulsion composition acting as a surfactant and surface coating for treatment of Eustachian tube dysfunction.

BACKGROUND OF THE INVENTION

The Eustachian tube (ET) is a very narrow air passage in the wall of a human's middle ear which connects it to the nasopharynx, a midline air filled space in the back of the nose. The tube is approximately 37 mm long and is slightly hourglass shaped, flattened anterior-posteriorly. The small lumen of the Eustachian tube permits the exchange of ambient gases between the middle ear and nasopharynx and the transport of middle ear secretions into the nasopharynx. The lateral one-third of the Eustachian tube (tympanic segment) is made of bone, while the medial two-thirds (pharyngeal segment) is cartilaginous. A constriction at the junction of the bony and cartilaginous segments, called the isthmus, may be as narrow as 1.0 mm by 1.5 mm. This tube regulates the intermittent exchange of air to or from the middle ear space to maintain equal pressure on both sides of the eardrum. The surface of the epithelium of the middle ear and Eustachian tube is covered by a raucous blanket, which is a defensive barrier against inhaled pollutants and a multitude of microorganisms. Middle ear secretions are normally eliminated through the ET.

In humans, the Eustachian tube is a very unique structure that enables the middle ear pressure to adapt to various altitude changes and, when closed, it prevents the endogenous intraoral sounds of respiration and vocalization from reaching the middle ear to compete with and mask out the environmental sounds for reception and relay to the inner ear.

Normally, the Eustachian tube maintains an isobaric relationship between the middle ear space and the ambient air exchanged within the nasal passages during breathing. The critical opening pressure for the tube to ventilate the middle ear chamber is related to the surface tension and diameter of the ET opening onto the lateral wall of the nasopharynx. This is modified by the rheological properties of the mucus blanket on the endothelial tissues. In its natural state, the Eustachian tube orifice is always closed, but may actively open spontaneously several times a minute or when swallowing or yawning. As integral part of the middle ear, the Eustachian tube functions to prevent and ameliorate the same inflammatory diseases such as otitis media etc. and its complications.

Blockage of the Eustachian tube isolates the middle ear space from the outside environment. The lining of the middle ear absorbs the trapped air and creates a negative pressure that pulls the eardrum inward. The eardrum is thin and pliable, like plastic wrap, and is densely innervated. When it becomes stretched inward, patients often experience pain, pressure, and hearing loss. Long-term blockage of the Eustachian tube leads to the accumulation of fluid in the middle ear space that further increases the pressure and hearing loss. This is called serous otitis media. Should bacteria contaminate this fluid, a middle ear infection may result, called acute otitis media.

Failure of the Eustachian tube to open during yawning, swallowing or barometric pressure changes between the middle ear and pharynx is called Eustachian tube dysfunction. This can occur when the lining of the nose becomes irritated and inflamed, narrowing the Eustachian tube opening or its passageway. Illnesses like the common cold or influenza are often to blame. Pollution and cigarette smoke can also cause Eustachian tube dysfunction. In many areas of the country, nasal allergy (allergic rhinitis) is the major cause of Eustachian tube dysfunction. For reasons that are unclear, the incidence of allergies is increasing in the United States. Obesity can also predispose a patient to Eustachian tube dysfunction because of excess fatty deposits around the passageway of the Eustachian tube. Rarely, Eustachian tube blockage may be the sign of a more serious problem such as nasal polyps, a cleft palate, or a skull base tumor.

Young children (especially ages 1 to 6 years) are at particular risk for Eustachian tube dysfunction, serous otitis media, and acute otitis media because they have very narrow Eustachian tubes. Also, they may have adenoid enlargement that can block the opening of the Eustachian tube. Since children in daycare are highly prone to getting upper respiratory tract infections, they tend to get more ear infections compared to children that are cared for at home.

The anatomy of the Eustachian tube in infants and young children is different than in adults. It runs horizontally, rather than sloping downward from the middle ear. The horizontal course of the Eustachian tube also permits easy transfer of bacteria from the nose to the middle ear space. This is another reason that children are so prone to middle ear infections.

Certain bacteria are reported to be the primary causes of acute otitis media (AOM) and are detected in about 60% of cases. The bacteria most commonly causing ear infections are: *Streptococcus pneumoniae* (also called *S. pneumoniae* or *pneumococcus*), the most common bacterial cause of acute otitis media, causing about 40% to 80% of cases in the U.S.; *Haemophilus influenzae*, the next most common culprit and is responsible for 20% to 30% of acute infections; and *Moraxella catarrhalis*, also a common infectious agent, responsible for 10% to 20% of acute infections. Less common bacteria are *Streptococcus pyogenes* and *Staphylococcus aureus*.

A serious sequalae of bacterial chronic otitis media includes otitis media with effusion (OME) that is associated with complications such as a ruptured tympanic membrane (TM). The failure of the Eustachian tube to expel or eliminate the natural secretions, microorganisms, biofilms and toxic products result in destruction of the tissues, TM rupture and hearing loss. When the fluid becomes infected the increased pressure is very painful and causes the delicate tympanic membrane to rupture releasing the toxins into the external ear canal for elimination In the past, antibiotics have been the mainstay of eliminating bacterial microorganisms by direct biochemical interaction. However, antibiotics can only treat the infection when and if the agent is capable of penetrating the biofilm barrier and altering the biochemistry of the microorganism internally.

Of note, about 15% of these bacteria are now believed to be resistant to the first-choice antibiotics. With the overuse of antibiotics and the development of resistance by microorganisms, such treatment has become less effective and frequent side effects have become common.

More recently, because the chemical structure of the newer anti-infective agents are more complex, antibiotics are not absorbable in the gastrointestinal tract, necessitating that the medication be administered by intravenous injection which is further associated with serious side effects such as ototoxicity, hearing loss and tinnitus, and allergic reactions. Scientific studies have identified prenatal markers, such as smoking, that predispose the infant to develop middle ear infections.

Various medical treatments other than antibiotics are utilized to alleviate the symptoms of ETD. In many cases, leaving it alone without any specific treatment is sufficient as the condition may only be temporary as the result of a cold or other respiratory disease. Swallowing and chewing are encouraged to manipulate the tissues surrounding the Eustachian tube thereby promoting the opening of the tube to equalize pressure to the middle ear. Self-inflation can be accomplished by doing a gentle Valsalva maneuver to force air up into the Eustachian tube. However, blowing too forcibly can make the condition worse by forcing fluids and bacteria from the throat into the tube. These procedures may not be sufficient to provide the individual with the length and degree of relief desired.

Synthetic and natural (pork or beef lung) pulmonary surfactant compounds have been in use in neonatology since the early 1980's. Tracheal administration of surfactant to premature infants with respiratory distress syndrome improves lung compliance, opens small air passages and has significantly improved life expectancy. Studies in the 1960's were unsuccessful because isolated surfactant proteins alone were being used. It was not until the addition of the emulsifier/spreading agent phosphatidylglycerol, derived from egg lecithin, that efficacy was finally demonstrated. Emulsifiers not only distribute pulmonary surfactant but also change its physical properties to be more fluid.

In animal studies, bacteria are injected into the middle ear space to increase Eustachian tube opening pressure. Nebulized bovine pulmonary surfactant compound administered intranasally to these animals demonstrated improved clearance of fluid from the middle ear, thus decreasing Eustachian tube opening pressure. However, individuals with allergies to beef or pork protein may suffer complications from this natural surfactant therapy, and the method of nebulized administration may be cost prohibitive for widespread use.

Medical professionals can also recommend or prescribe a variety of drugs to treat ETD. Decongestants, either orally or nasally, may promote the opening of the Eustachian tube. Nasal corticosteroids can relieve tissue inflammation, one of the major causes of ETD. Antihistamines may reduce the amount of rhinorrhea and post-nasal drainage that may contribute to ETD. Use of over-the-counter or prescription drugs, which are absorbed into the user's system, may not be tolerated by the individual because of various side effects.

It is therefore desirable to provide a composition for the treatment of Eustachian tube dysfunction that is effective in unblocking a clogged Eustachian tube and that is well tolerated without undesirable side effects.

SUMMARY OF THE INVENTION

The present disclosure is generally directed to a method for applying a surfactant to the pharynx opening of the Eustachian tube in the treatment of Eustachian tube dysfunction. The method includes placing the person's body in a position for coating the person's pharynx. A composition of simethicone emulsion diluted in an aqueous carrier is introduced. The simethicone composition is then allowed to coat the person's pharynx.

In one aspect of the invention the position in which the person is placed is lying on one of the person's left and right sides, the side being a side affected by Eustachian tube dysfunction.

In another aspect, the simethicone composition is introduced through the nasal cavity of the same side on which the person is lying and allowing the introduced simethicone composition to drain from the nasal cavity and coat the person's pharynx on the side of which the person is lying.

In yet other aspects, the manner of composition introduction is by nasal spray or by instilled drops.

In yet a further aspect of the invention, the introduced simethicone composition is in a concentration of about 0.05% to 0.65% wt/vol.

In a further aspect of the invention, the simethicone from the Eustachian tube opening is removed by orally administering a liquid emulsifier. The emulsifier being either soy lecithin or egg lecithin.

In another aspect, the position in which the person is placed is an upright position.

In a further aspect, the simethicone composition is introduced orally.

In yet a further aspect, the orally introduced simethicone composition is in a concentration of about 0.05% to 30% wt/vol.

In another aspect of the invention, a method of treating Eustachian tube dysfunction in a person includes the steps of combining into a composition, a simethicone emulsion with a second active ingredient. The combined simethicone and active ingredient is orally introduced to the person. The simethicone composition is then allowed to coat the person's pharynx.

Another aspect of the invention is combining the simethicone emulsion with xylitol in a chewing gum.

Yet a further aspect of the invention is compounding the simethicone emulsion with a medication. The medications can be selected from the group of a steroid, a non-steroidal anti-inflammatory, gold nanocrystals, antibiotic, and antihistamine.

Another aspect of the invention is a composition for topically treating Eustachian tube dysfunction wherein the composition includes an aqueous carrier and a simethicone emulsion in a concentration of about 0.05% to 30%.

A further aspect of the invention includes the aqueous carrier being distilled water or a saline solution.

In yet another aspect of the invention the simethicone emulsion includes simethicone USP, a food grade emulsifier, sodium carboxymethylcellulose, and sorbic acid.

BRIEF DESCRIPTION OF THE DRAWINGS

The invention will now be described, by way of example, with reference to the accompanying drawings, where like numerals denote like elements and in which.

Like reference numerals refer to like parts throughout the various views of the drawings.

DETAILED DESCRIPTION OF THE INVENTION

Figure 1:
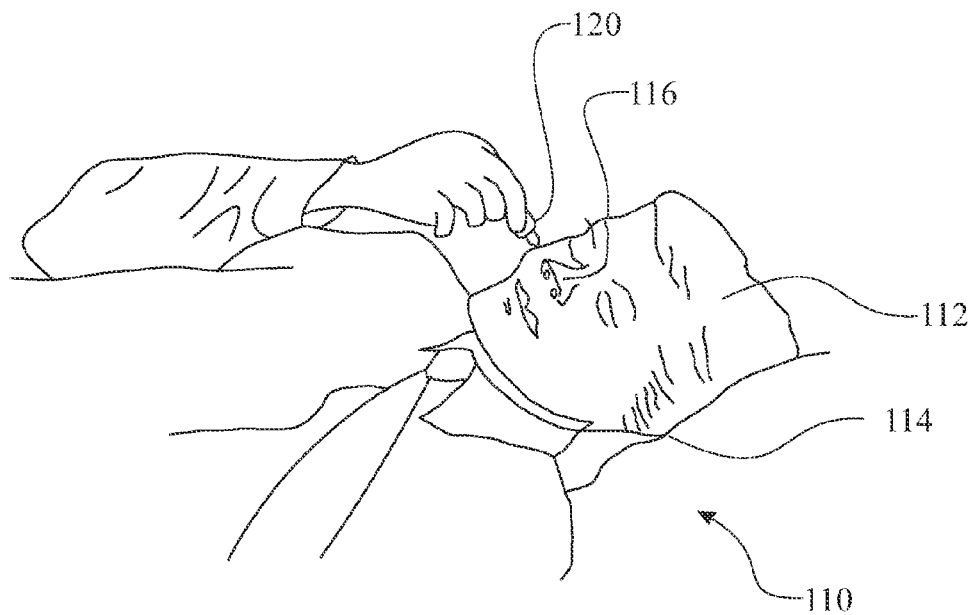
FIG. 1 presents a person afflicted with Eustachian tube dysfunction lying on one side for treatment according to the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The Eustachian tube is a small tube-like canal which connects the inner part of the ear called the middle ear to the back of the nose and upper throat area known as the pharynx with the stoma (opening) of the tube being located in the pharynx. The tube stoma in the pharynx is normally in a closed position to prevent food particles and mucous from being forced into the tube as a result of blowing one's nose, coughing or other similar bodily functions. The function of the Eustachian tube is to equalize the air pressure within the middle ear and the pressure outside it. While a positive pressure differential within the middle ear is generally easily relieved, most individuals having difficulty with Eustachian tube dysfunction primarily experience difficulty when there is a negative pressure differential within the middle ear and the tube opening in the pharynx failing to open to equalize the pressure. The greater outside ambient air pressure compared to the pressure within the inner ear further contributes to the pharynx stoma remaining closed.

Research has shown that the Eustachian tube (ET) in humans is lined with a substance that lowers surface tension and thus facilitates the opening of the Eustachian tube and aeration of the middle ear. However, when a human suffers from ETD, oftentimes a mucosal film is found on the surface of the pharynx and over the stoma of the Eustachian tube. The surface tension of this mucosal film can be sufficiently great as to hinder or prevent the tube from opening to aerate the inner ear and equalize the negative pressure differential.

Poly (dimethylsiloxane), silicon dioxide, most commonly known as Simethicone, is a well known surfactant that acts as an anti-foaming agent to decrease the surface tension of gas bubbles, causing them to combine into larger bubbles. Simethicone (chemical structure illustrated below) has long been used in humans to treat intestinal gas by causing smaller intestinal gas bubbles to combine into large bubbles, which are more easily passed by burping. While Simethicone does not prevent the formation of gas, it increases the rate at which the gas exits the body. Simethicone is not absorbed by the body into the bloodstream, and is therefore considered relatively safe.

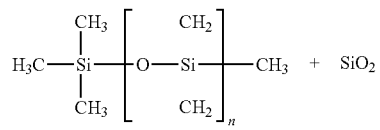

Poly (dimethylsiloxane), silicon dioxide

Since simethicone polymer is an inert substance, it is not absorbed, will not react with other substances, and is generally considered to be safe. Simethicone emulsion contains water, simethicone USP, food grade emulsifiers, sodium carboxymethylcellulose (a thickener) and sorbic acid. Removing simethicone polymer from the Eustachian tube opening may be accomplished by dilution with nasal saline lavage, or administering an emulsifier alone by mouth such as liquid soy lecithin or egg lecithin.

Simethicone emulsion has been safely administered to newborn infants at a dose of up to 6 drops twelve times daily by mouth. Any complications would come from the penetration of the polymer to below the mucosal surface as during a traumatic injury, which would not ordinarily be expected. Studies are currently being conducted to determine simethicone emulsion's effect on Eustachian tube opening pressure; however clinical application has shown anecdotal reduction in ear pain to within 30 minutes of oral administration, and reduced incidence of ear infection.

Simethicone polymer coating of mucosal pharyngeal structures such as the larynx, vocal cords, nasal cavity, sinuses and Eustachian tube may offer conditioning effects that are not yet fully understood. Decreasing mucosal surface tension may produce a relative increase in submucosal vascular oncotic pressure therefore drawing fluid into blood vessels to relieve symptoms of rhinorrhea or excess mucous. Polymer spread to within the Eustachian tube may act as a thin layer stent preventing the stoma from complete closure. This effect could decrease Eustachian tube opening pressure by having a small amount of polymer between mucosa-to-mucosa contact points. Air and fluid would still flow through the open Eustachian tube to maintain a middle ear environment that is not conducive to bacterial overgrowth or barotrauma.

The surface tension reducing characteristics of Simethicone in combination with its non-absorbability can also be beneficial for treating, with minimal side effects, conditions such as Eustachian tube dysfunction wherein reduction of the surface tension of the mucosal film can aid in allowing the tube stoma in the pharynx to more easily open and equalize the pressure within the middle ear. However, an appropriate delivery mechanism must be utilized since Simethicone, when used to control intestinal gas, is normally introduced orally through the swallowing or chewing of solid tablets.

An exemplary embodiment Simethicone composition for use in treatment of the symptoms of ETD includes a simethicone emulsion diluted in an aqueous carrier such as distilled water or saline solution. The liquid composition comprises 0.05% to 0.65% Simethicone by weight or volume since concentrations exceeding 0.65% may present a risk of olfactory nerve damage. The simethicone composition is introduced through the nasal cavity by nasal spray or instilled drops. Alternately, 2 to 6 drops of a composition of simethicone emulsion in the concentration of 0.05% to 30% by weight or volume diluted in an aqueous carrier is introduced orally. Alternately, a composition of simethicone emulsion in the form of a tablet or thin strip is introduced orally. Repeat administration is recommended once daily for two weeks during upper respiratory congestion or ear discomfort for children over 6 months of age and adults. To maintain reduced Eustachian tube opening pressure, administration may continue once every 3 to 4 days. Simethicone emulsion could also be administered 30 minutes prior to an anticipated period of environmental barometric pressure change in which ear discomfort, pain or barotrauma would be expected.

Figure 2:
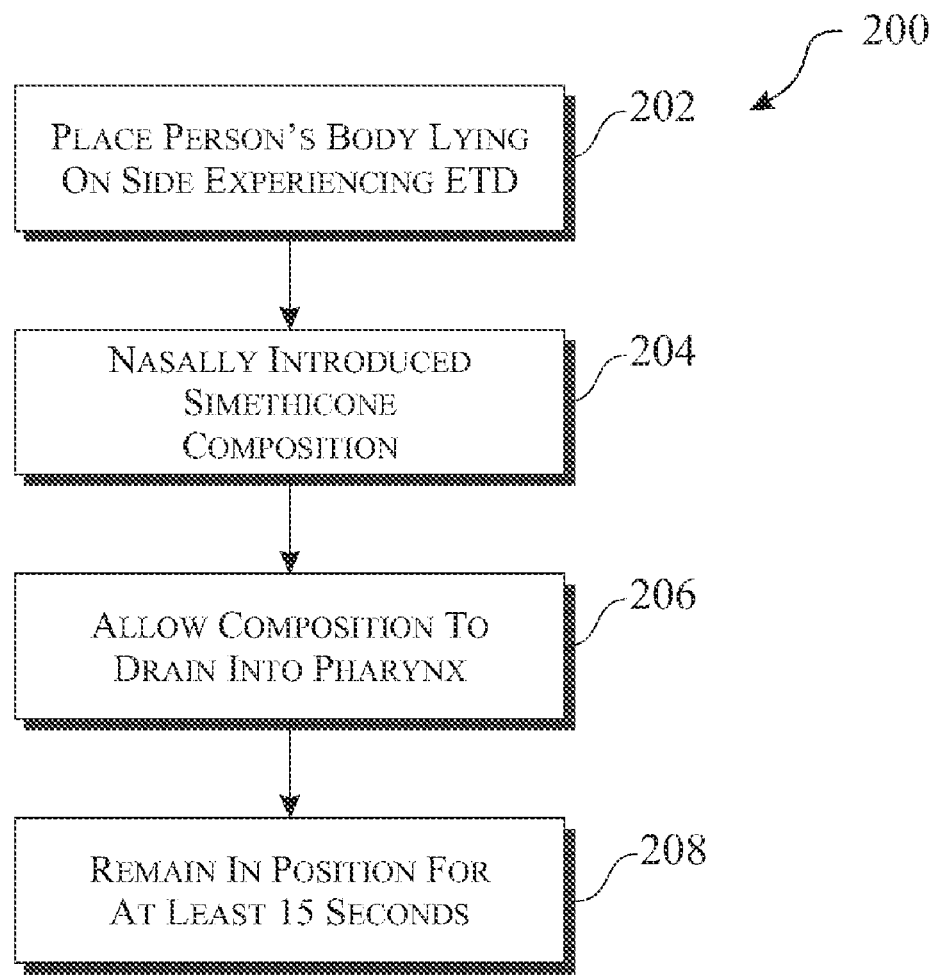
FIG. 2 presents a block diagram of a method for treating Eustachian tube dysfunction using a simethicone composition.

Referring to FIG. 1 illustrating the positioning of a patient 110 for administration of the composition and to FIG. 2 depicting in block form an exemplary administration protocol, the patient 110 afflicted with Eustachian tube dysfunction, in block 202, FIG. 2, lies down on either the patient's left or right side. If the left Eustachian tube is affected, the patient 110 lies on their left side, and similarly for the right side. The patient 110 orients his or her head 112 between 45 to 60 degrees above horizontal and turned 45 to 60 degrees toward the affected ear 114. FIG. 1 depicts the affected ear 114 as the left ear. Those practiced in the art will recognize that the procedure for the right ear is similar but oppositely oriented. This orientation of the patient's head 112 positions the Eustachian tube stoma lower than the ipsilateral nostril 116.

In block 204, FIG. 2, 2-4 drops of the Simethicone composition is introduced in the ipsilateral nostril (left nostril when treating the left Eustachian tube stoma) by use of a dropper 120. In block 206, FIG. 2, gravity allows the drops to flow or drain to the back of the nose and into the pharynx to coat the area around the tube stoma. Sniffing will draw the drops further into the nasal passage to the Eustachian tube stoma before the semi-permeable membrane lining of the nasal passage can absorb them. Alternatively, a nasal mister can be utilized in lieu of dropper 120 to introduce the Simethicone composition into the nasal cavity whereupon the subsequent procedure is identical to the use of dropper 120 and the introduction of drops of the Simethicone composition. Once the composition drops have been instilled into the nasal cavity the patient, in block 208, FIG. 2, remains lying on his or her side for at least 15 seconds prior to arising or shifting to treat the opposite Eustachian tube stoma.

The simethicone emulsion composition is allowed to coat the individual's pharynx and related structures by diffusion. An emulsifier in the composition reduces surface tension along the mucous membranes thus spreading simethicone throughout. Simethicone polymer is distributed throughout the mucous membranes including the opening of the Eustachian tube where the polymer reduces surface tension and reduces Eustachian tube opening pressure. Simethicone polymer may also be distributed along the intraluminal surface of the Eustachian tube. Inside the tube, polymer reduces Eustachian tube opening pressure by partially impeding Eustachian tube closure as a semi-fluid stent.

Due to inert properties of simethicone emulsion, it can be administered concomitantly or compounded with many other active ingredients. One such ingredient Xylitol is a sugar shown to prevent otitis media when taken as a chewing gum. Simethicone emulsion may also be administered concomitantly or compounded with other medications such as a steroid, non-steroidal anti-inflammatory, gold nanocrystals, antibiotics or antihistamines to facilitate distribution of that medication throughout the pharynx and related structures. Simethicone emulsion may also be administered concomitantly or compounded with radio opaque dyes such as a barium sulfate or diatrizoic acid for radiographic imaging of the pharyngeal structures. Studies need to be conducted in order to demonstrate effectiveness of other active ingredients co-administered with simethicone emulsion.

In addition to the treatment of Eustachian tube dysfunction, use of the nasally instilled Simethicone liquid composition can be used to prevent or treat ear and sinus infections, ear dysfunction during airline travel or diving, and improve a person's sense of smell and hearing. Simethicone can also be added to Fluticasone Propionate Nasal Spray (know by the trade name Flonase) or other nasal steroids or antihistamines.

Alternatively, a formulation including a higher concentration of Simethicone can be utilised for oral administration. Such a formulation is marketed under the trade name Mylicon® (manufactured by Johnson & Johnson—Merck Consumer Pharmaceuticals Co.) and is generally given to infants under six months of age to relieve the discomfort of infant gas frequently caused by swallowed air or by certain infant formulas. While this formulation (Mylicon®) has a higher concentration of Simethicone (20 mg per 0.3 ml), oral administration bypasses the nasal cavities and thus averts the risk to the olfactory nerves previously noted. Mylicon® as orally administered can treat Eustachian tube dysfunction with the additional benefit of preventing potential ear infections.

For oral administration, the patient assumes a lying down position biasing his/her head to a side of the body desired to be treated (right or left). The dosage (4-6 drops) of Mylicon® is orally administered while in this generally supine position thereby allowing the Mylicon® drops to diffuse to the posterior nasal pharynx where the Eustachian tube stoma is located. The patient remains lying in this position for at least 15 seconds prior to arising to allow proper diffusion of the Mylicon®. The patient can then arise or shift to the opposite side to treat the opposite side of the posterior nasal pharynx. With regard to oral administration, the Mylicon® can either be swallowed or gargled and then spit out.

With decreased mucous production, the mucosa may be more exposed to the harmful effects of toxins contained in cigarettes; therefore, smoke related illnesses including cancer might be increased by using surfactants and smoking. Individuals who use a pharyngeal surfactant should not smoke for at least one week after surfactant administration.

As an alternative to utilizing Simethicone as a surfactant, nasal bacteria can be genetically engineered or infused with a developed plasmid such that when the bacteria start to overgrow, they either secrete a natural surfactant or release a surfactant from dead bacteria thereby preventing the development of ear or sinus infections in the patient.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method for treating Eustachian tube dysfunction in a person, comprising the steps of:
    placing the person's body in a position to receive a composition for coating the person's pharynx;
    introducing a composition of simethicone emulsion diluted in an aqueous carrier into the person's pharynx;
    allowing the simethicone composition to coat the person's pharynx; and
    removing the simethicone from the Eustachian tube opening by orally administering a liquid emulsifier.

2. The method according to claim 1 wherein the liquid emulsifier is selected from the group consisting of soy lecithin and egg lecithin.

3. A method for treating Eustachian tube dysfunction in a person, comprising the steps of:
    combining a simethicone emulsion with xylitol into a composition in the form of a chewing gum;
    orally introducing the composition to the person; and
    allowing the composition to coat the person's pharynx.

* * * * *